(12) United States Patent
Yokokawa et al.

(10) Patent No.: US 6,646,271 B2
(45) Date of Patent: Nov. 11, 2003

(54) METHOD AND APPARATUS FOR READING FLUORESCENCE

(75) Inventors: Naoki Yokokawa, Kanagawa (JP); Mitsuhiro Tachibana, Kanagawa (JP)

(73) Assignee: Hitachi Software Engineering CO, Ltd., Kanagawa (JP)

( * ) Notice: Subject to any disclaimer, the term of this patent is extended or adjusted under 35 U.S.C. 154(b) by 137 days.

(21) Appl. No.: 09/998,527

(22) Filed: Nov. 28, 2001

(65) Prior Publication Data

US 2002/0121611 A1 Sep. 5, 2002

(30) Foreign Application Priority Data

Nov. 28, 2000 (JP) .......................... 2000-361237

(51) Int. Cl.⁷ .............................................. G01N 21/64
(52) U.S. Cl. ................... 250/458.1; 250/459.1
(58) Field of Search ............................ 250/458.1, 459.1

(56) References Cited

U.S. PATENT DOCUMENTS

| | | | | |
|---|---|---|---|---|
| 5,091,652 A | * | 2/1992 | Mathies et al. ............ | 250/458.1 |
| 5,459,325 A | | 10/1995 | Hueton et al. ............ | 250/458.1 |
| 6,078,390 A | | 6/2000 | Bengtsson .................. | 356/318 |
| 6,329,661 B1 | * | 12/2001 | Perov et al. ............... | 250/461.2 |
| 6,407,395 B1 | * | 6/2002 | Perov et al. ............... | 250/458.1 |
| 6,471,916 B1 | * | 10/2002 | Noblett ...................... | 422/82.08 |

OTHER PUBLICATIONS

M. Neumann et al., Capillary array scanner for time–resolved detection and identification of fluorescently labelled DNA fragments, Journal of Chromatography A, 871 (2000) 299–310.

* cited by examiner

*Primary Examiner*—David Porta
*Assistant Examiner*—Christine Sung (57) ABSTRACT

The present invention aims at minimizing the influence of residual fluorescence emitted from adjacent spots, upon reading time-resolved fluorescence.

The path of laser beam scan is set to be intermittent such that residual fluorescence from adjacent spots gives no effect. In other words, the spots are read in a skipping manner.

14 Claims, 7 Drawing Sheets

Prior Art

METHOD AND APPARATUS FOR READING FLUORESCENCE

PRIORITY INFORMATION

This application claims priority to Japanese Application Serial No. 361237/2000, filed Nov. 28, 2000.

FIELD OF THE INVENTION

The present invention relates to a method and an apparatus for determining an amount of light for each of a plurality of microspots arranged on a plane. More particularly, the present invention relates to a method and an apparatus for reading fluorescence on a biochip where biological substances such as DNAs or proteins labeled with a time-resolved fluorescent substance are arranged as a high-density spot array.

BACKGROUND ART

Currently-practiced methods for analyzing chemical and physical properties of biological substances such as DNA and proteins often utilize fluorescence. These methods use a biochip on which biological substances such as DNAs or proteins that are labeled with a fluorescent substance marker are arranged as a high-density microspot array. In order to read these spots, a fluorescence reading apparatus is necessary which scans the spots with a laser beam to excite the fluorescent label existing in each spot on the biochip, thereby reading the excited fluorescence from each spot.

Figure 7:
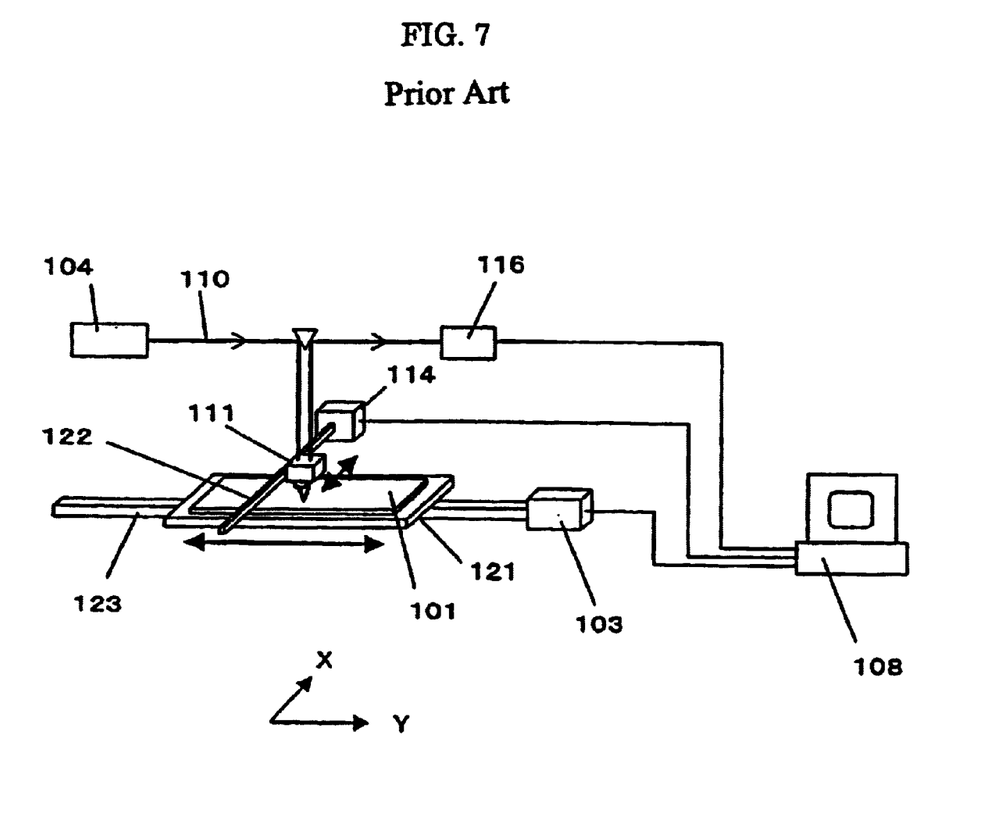
FIG. 7 is a schematic view showing a conventional fluorescence reading apparatus.

FIG. 7 is a schematic view of a conventional fluorescence reading apparatus. A biochip 101 is a rectangular glass plate whose surface is provided with DNAs labeled with fluorescent substance Cy3 (excitation wavelength: 552 nm, fluorescence wavelength: 565 nm, duration: 1.3 ns) which are aligned as microspots in a matrix along x- and y-directions. The biochip 101 is placed on a stage 121 which travels stepwisely in the y-direction by a y-direction driving motor 103. A reading head 111 placed above the biochip 101 is continuously driven in the x-direction by a x-direction driving motor 114. A laser beam 110 emitted from a laser light source 104 is radiated on the biochip 101 via the reading head 111. The fluorescence generated on the biochip 101 is captured by a photomultiplier 116 via the reading head 111. The laser light source 104 emits a laser beam at a wavelength of 552 nm, a wavelength appropriate to excite the marker Cy3.

Upon reading the biochip 101, the reading head 111 is continuously transferred in the x-direction along an x-axis rail 122 by the x-direction driving motor 114 under the control of a control computer 108. Similarly, the stage 121 holding the biochip 101 is transferred stepwisely in the y-direction along a y-axis rail 123 under the control of the control computer 108.

FIGS. 8A to 8E are schematic diagrams showing the order for reading the respective spots on the biochip 101 according to a conventional reading. The spots are arranged in a two-dimensional matrix along x- and y-directions. A black dot represents a spot whose fluorescence has been read, while a white dot represents a spot whose fluorescence has not yet been read.

Figure 8A:
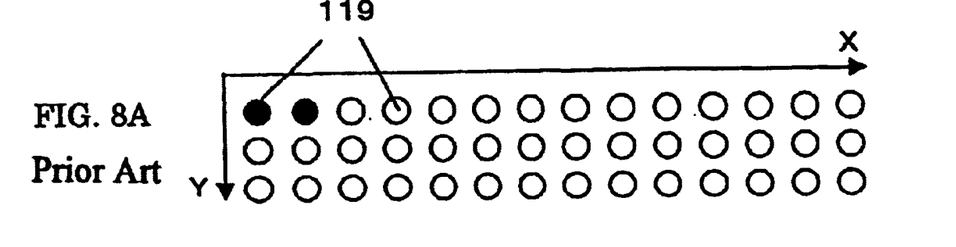
FIGS. 8A to 8E are diagrams for illustrating an order for reading spots according to a conventional method.
Figure 8B:
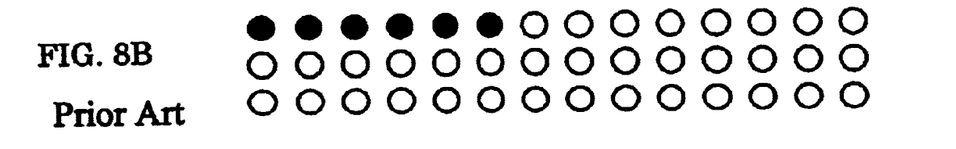
Figure 8C:
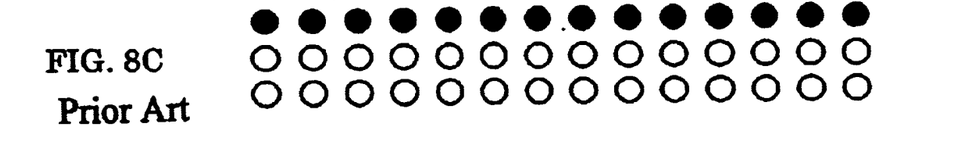
Figure 8D:
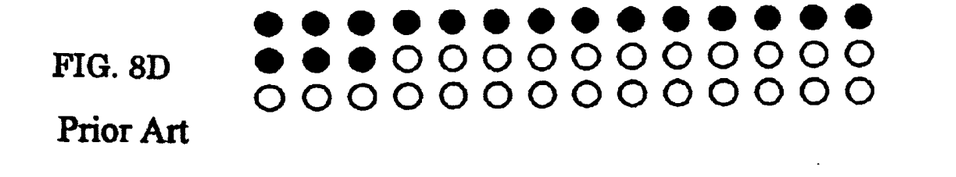
Figure 8E:
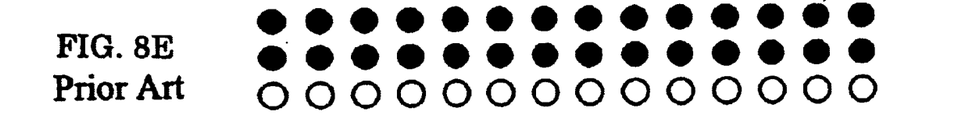

As shown in FIGS. 8A to 8C, the spots 119 on the biochip 101 are irradiated with the laser beam at a constant rate. Irradiation by the laser beam as well as reading the fluorescence resulting from the laser beam irradiation take place simultaneously and continuously. As shown in FIG. 8C, once scanning for a single row in the x-direction is completed, the reading head 111 returns to the left end of the same row. Then, the stage 121 is transferred stepwisely to send the biochip 101 in the y-direction for one resolution distance. Then, as shown in FIGS. 8D and 8E, the next row is scanned continuously in the x-direction. By repeating this series of steps, the entire area of the biochip 101 is completely scanned.

When a fluorescent substance such as Cy3 is used to label a biological substance, fluorescence should be read while radiating excitation light since the duration of fluorescence is as short as a few ns. Although the fluorescence capturing member is provided with an optical filter or the like that only passes the wavelength of the fluorescence and blocks the excitation light, it is hard to detect only the fluorescence by completely blocking the excitation light since the fluorescent intensity of the fluorescent label is as extremely weak as about $1/1000000$ the intensity of the excitation laser beam.

Thus, a time-resolved fluorescent substance such as europium (duration: 400 $\mu$s) with a very long fluorescent duration as compared to, for example, Cy3 (duration: 1.3 ns) may be used. The time-resolved fluorescent substance excited by laser beam irradiation retains the excitation state even after the laser beam irradiation depending on the relative duration. By utilizing this property, the laser beam irradiation and the fluorescence reading may be performed asynchronously so that fluorescence reading takes place after the excitation light irradiation, thereby preventing deterioration of the S/N ratio caused by capturing the excitation laser beam during the fluorescence reading. However, even when such a time-resolved fluorescent substance is employed as a label, the S/N ratio of the fluorescence detection of the spots can be poor since the conventional fluorescence reading apparatus sequentially reads the time-resolved fluorescent substances on the biochip along the laser beam irradiation path, and thus residual fluorescence resulting from the longer duration may become a noise and interfere with the reading of the adjacent spot.

In view of the above-mentioned problems, the present invention has an objective of providing a method and an apparatus for reading fluorescence, with which deterioration of the S/N ratio caused by residual fluorescence from an adjacent spot resulting from the use of the time-resolved fluorescent label can be prevented, thereby realizing fluorescence reading at a high S/N ratio.

SUMMARY OF THE INVENTION

In order to achieve the above-mentioned objective, the method for reading fluorescence of the present invention reads fluorescence by radiating excitation light on a plurality of spots arranged at predetermined intervals each containing a substance labeled with a time-resolved fluorescent substance and detecting fluorescence generated from each of the plurality of spots, the method comprising: a first step of irradiating a first spot with excitation light for a predetermined time; a second step of detecting fluorescence generated from the first spot after the irradiation with the excitation light; a third step of irradiating a second spot with excitation light, which is distanced from the first spot by a distance that is two or more times the distance between adjacent spots; and a fourth step of detecting fluorescence generated from the second spot after the irradiation with the excitation light, wherein, the third and fourth steps are repeated to detect fluorescence from all of the spots.

The plurality of spots may be arranged in a two-dimensional matrix along x- and y-directions, in a concentric pattern or in a spiral pattern. A second spot, which is distanced from the first spot by a distance two or more times the distance between the spots, is typically two spots away from the first spot that has just underwent fluorescence detection.

The time-resolved fluorescent substance according to the present invention refers to a fluorescent substance that lasts for a duration of 10 ns or longer. Examples of the time-resolved fluorescent substance include europium (excitation wavelength: 326 nm, fluorescence wavelength: 612 nm, duration: 400 µs) and luciferin. In order to enhance the detection sensitivity, longer duration is desirable.

According to above-described method, undesirable capture of the excitation light as well as undesirable capture of the time-resolved fluorescence emitted from already-detected spots can be avoided, thereby greatly improving the SIN ratio of fluorescence detection.

A method according to the present invention reads fluorescence by radiating excitation light on a plurality of spots arranged in a line at predetermined intervals each containing a substance labeled with a time-resolved fluorescent substance and detecting fluorescence generated from each of the plurality of spots, wherein an operation of radiating excitation light to a spot for a predetermined time and thereafter detecting fluorescence generated from the spot is performed sequentially for every nth spots (where n is an integer of 2 or higher), and when the operation reaches the end of the line, the operation goes back towards the top of the line and is repeated for every nth spots (where n is an integer of 2 or higher) starting from a spot that has not yet undergone fluorescence detection.

Furthermore, a method according to the present invention reads fluorescence by radiating excitation light on a plurality of spots arranged in a line at predetermined intervals each containing a substance labeled with a time-resolved fluorescent substance and detecting fluorescence generated from each of the plurality of spots, wherein an operation of radiating excitation light to a spot for a predetermined time and thereafter detecting fluorescence generated from the spot is performed sequentially for every second spots, and when the operation reaches the end of the line, the operation goes back towards the top of the line and is repeated for the remaining spots.

According to the above-described method for reading fluorescence, the substance labeled with the time-resolved fluorescent substance may be a biological substance.

An apparatus of the present invention reads fluorescence by detecting fluorescence from a plurality of spots arranged on a substrate each containing a substance labeled with a time-resolved fluorescent substance, the apparatus comprising: a stage for holding the substrate; a laser light source; a reading head movable in a two-dimensional manner relative to the substrate, the reading head provided with an excitation light optical system for irradiating the spots on the substrate with a laser beam emitted from the laser light source and a light capturing optical system for capturing fluorescence generated from the spots; an optical detector for detecting fluorescence captured by the light capturing optical system; a driver for driving the stage and the reading head relative to each other; and a controller for controlling the laser light source, the light detector and the driver, wherein the controller controls the driver such that the reading head is aligned above each of the spots on the substrate in a skipping manner, and controls the laser light source and the light detector such that a spot below the reading head is irradiated with a laser beam for a predetermined time and thereafter fluorescence generated from the irradiated spot is detected.

Alignment in a skipping manner means to first target one spot to perform fluorescence detection, and then to target a next spot that is not directly adjacent to the first spot (typically, one after the spot directly adjacent to the first spot) to perform fluorescence detection. Owing to this skipping alignment (fluorescence detection in a skipping manner), capturing the excitation light as well as capturing the time-resolved fluorescence from already-detected spot can be avoided, thereby greatly enhancing the S/N ratio of the fluorescence detection.

Preferably, the irradiation light optical system and the light capturing optical system form a confocal optical system.

The driver may comprise a reading head driver for driving the reading head in one direction, and a stage driver for driving the stage in a direction generally perpendicular to the driving direction of the reading head.

The fluorescence reading apparatus of the invention is useful for reading a biochip provided with a plurality of spots containing biological substances labeled with a time-resolved fluorescent substance.

PREFERRED EMBODIMENTS OF THE INVENTION

Hereinafter, an embodiment for carrying out the present invention will be described in detail with reference to the accompanying drawings. Herein, a time-resolved fluorescence substance used as a label is europium having an excitation wavelength at 326 nm, a fluorescence wavelength at 612 nm, and duration of 400 µs. However, the present invention is equally applicable to other time-resolved fluorescent substances. The numerical values that appear in the present description are merely an illustration and by no means limit the present invention.

Figure 1:
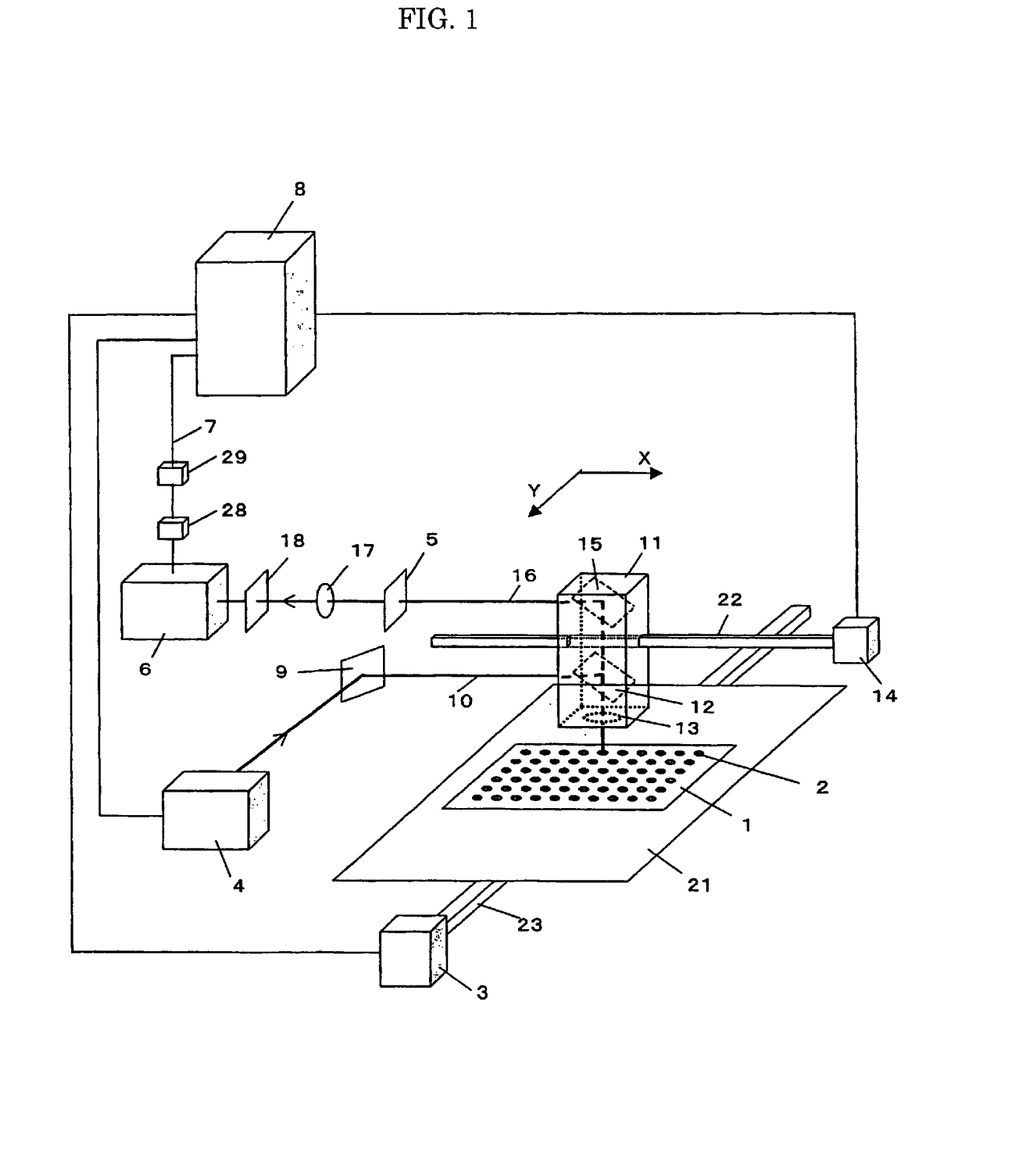
FIG. 1 is a schematic view showing an example of a fluorescence reading apparatus according to the present invention.

FIG. 1 is a schematic view showing an example of a fluorescence reading apparatus of the invention. A biochip 1 is, for example, a 25 mm×75 mm rectangular glass plate. The surface of the biochip 1 is provided with europium-labeled (time-resolved-fluorescent-substance-labeled) DNA microspots 2 each having a diameter of 50 µm arranged in a grid pattern in x- and y-directions and spaced by 100 µm from each other. The biochip 1 is held on a stage 21 which is driven stepwisely along a y-axis rail 23 by a y-direction driving motor 3. A reading head 11 incorporating parts of a laser beam irradiation optical system and a fluorescence capturing optical system is linearly transferred in the x-direction along a x-axis rail 22 by a x-direction driving motor 14 as a stepping motor. The x- and y-direction driving motors 14 and 3 are controlled by a control computer 8.

A laser beam at a wavelength of 326 nm emitted from a laser light source 4 changes its course by a total reflection mirror 9 to proceed along an optical path 10 of irradiation light which is set parallel to the transfer direction of the reading head 11 represented by an arrow X, thereby being incident upon a dichroic mirror 12. Since the dichroic mirror 12 is designed to reflect the excitation laser beam at a wavelength of 326 nm and allow light of other wavelengths to pass through, the incident laser beam that has traveled along the optical path 10 of the irradiation light is totally reflected downward in the figure, thereby being incident upon a confocal objective lens 13. The confocal objective lens 13 is arranged within the reading head 11, spaced from the surface of the biochip 1 for its focal distance, to narrow down the laser beam reflected off the dichroic mirror 12 and radiate it on the surface of the biochip 1 as microspot light as well as to converge light from the surface of the biochip 1.

When light at a wavelength other than about 326 nm is generated on the surface of the biochip 1, the light passes through the confocal objective lens 13 and passes through the dichroic mirror 12 in the upward direction in the figure and be incident upon the total reflection mirror 15. Here, the course of light is changed to proceed along an optical path 16 of detection light which is parallel to the optical path 10 of irradiation light of the laser beam, whereby the light is output from the reading head 11. The light output from the reading head 11, proceeding along the optical path 16 of the detection light passes through a filter 5 that has a band-pass property for around 612 nm (wavelength of europium), a diaphragm lens 17 and a pinhole plate 18, and be incident upon a photomultiplier 6. The photomultiplier 6 detects photon and generates a TTL level pulse (L level: 0 V, H level: 2.5 V). The number of pulses output from the photomultiplier 6 per unit time is proportional to the number of photons. The pulse output from the photomultiplier 6 as a photon pulse 7 of europium is amplified by an amplifier 28, converted into a digital signal by an A/D converter 29 and sent out to the control computer 8.

Figure 2A:
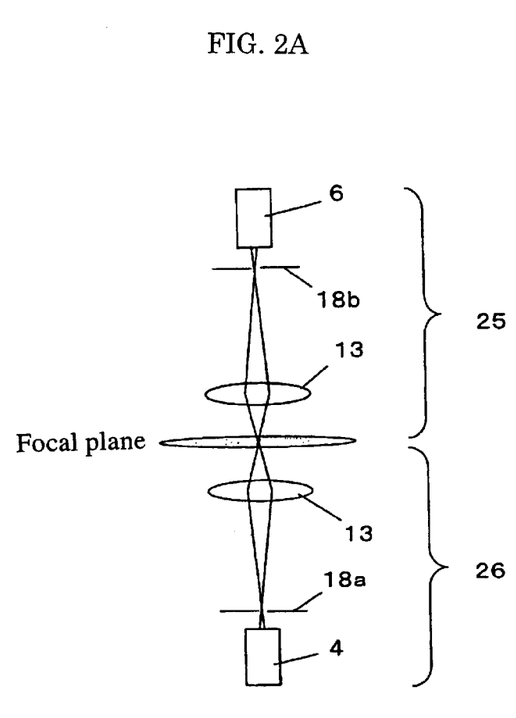
FIGS. 2A and 2B are illustrative diagrams of a confocal optical system.
Figure 2B:
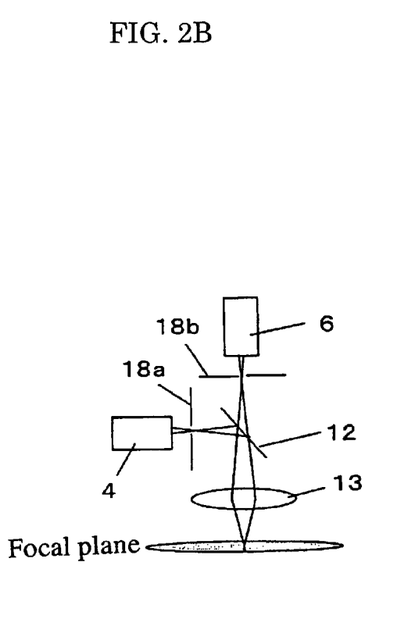

The present invention employs a confocal optical system for radiating excitation light and for converging fluorescence. Confocal refers to a state where the light source and the light detector are in an optically conjugate positional relationship with respect to the objective lens, namely, light emitted from a point of the light source is converged on a point of the detector. In order to establish this state, as shown in FIG. 2A, completely equivalent lens systems are provided on both irradiation side 26 and detection side 25 and pinholes 18a and 18b are provided in front of the light source 4 and the detector 6, respectively, whereby the lens systems serve as confocal points. However, in practice, the dichroic mirror 12 is provided in order to use a lens system that serves for both the irradiation side and the detection side as shown in FIG. 2B. Due to this structure, the present confocal system only captures fluorescence from a specimen or reflected light (the transmitted light image is not the confocal image). Since the light source and the detector are correlated to each other via corresponding points, only information of points is obtained for the sample. Thus, in order to obtain two- or three-dimensional information, the sample needs to be scanned inside.

The laser light at a wavelength of 326 nm output from the laser light source 4 scans over the biochip 1 in the x-direction with the reading head 11 being driven with the x-direction driving motor 14. When the laser light is radiated to a spot containing europium-labeled DNA, europium is excited to generate fluorescence. The amount of the generated fluorescent light depends on the amount of the fluorescent substance (in this example, europium) contained in the spot.

Figure 3:
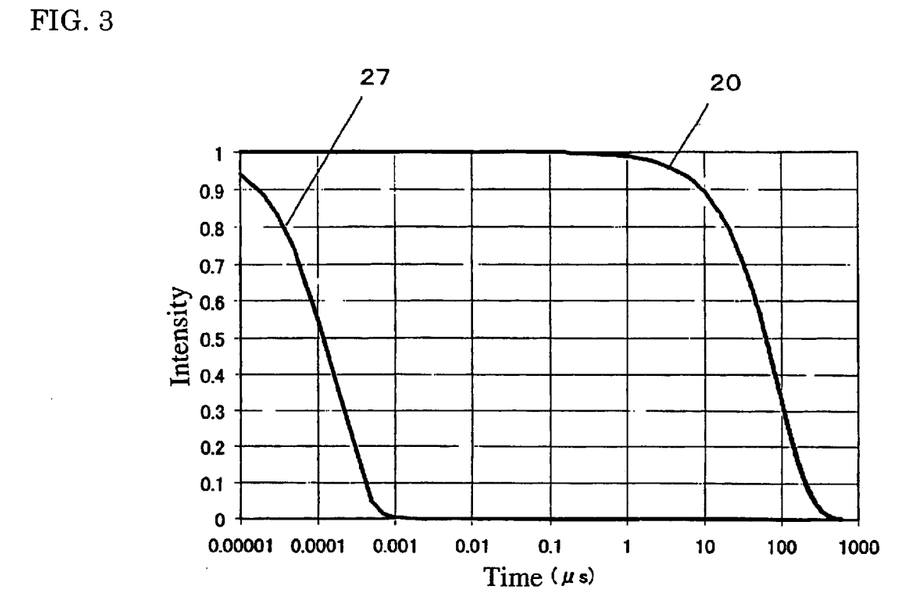
FIG. 3 is a graph showing attenuation waveforms of fluorescence from Cy3 and europium.

FIG. 3 is a graph showing attenuation waveforms of fluroescence 27 emitted from Cy3 and time-resolved fluorescence 20 emitted from europium. The horizontal and vertical axes represent time after the excitation light irradiation and a fluorescent intensity, respectively. The fluorescent intensity is normalized such that the fluorescent intensity immediately after the excitation light irradiation is 1. As shown in FIG. 3, a time-resolved fluorescence substance such as europium maintains the excitation state for a while even after the laser beam irradiation. The present invention utilizes this property to perform the laser beam irradiation and the fluorescence reading in an asynchronous manner. Accordingly, unlike conventional Cy3 or other fluorescent substances, the excitation laser beam can be prevented from being detected as noise upon fluorescence reading, and thus a higher S/N ratio than that obtained with conventional fluorescence reading (S/N ratio: around 10) can be obtained.

However, the above-described property of the time-resolved fluorescence may deteriorate the S/N ratio upon fluorescence reading. When the adjacent spots on the biochip are sequentially read by the reading head 11 in the x-direction according to the conventional scan technique as shown in FIG. 8, residual fluorescence resulting from the long duration of the time-resolved fluorescence of the preceding is detected as noise.

Figure 4:
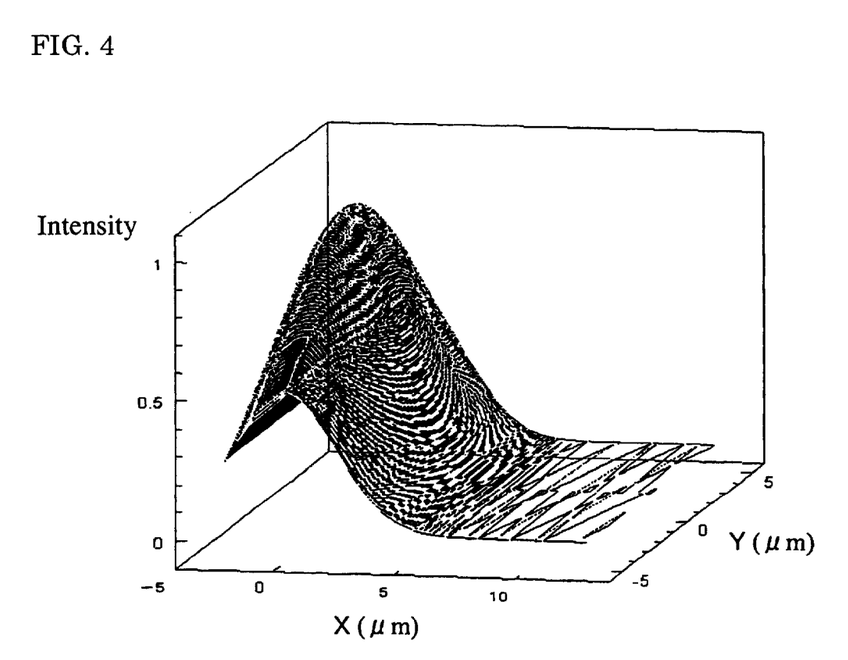
FIG. 4 is a graph showing a distribution of light detected with a confocal objective lens.

FIG. 4 is a graph showing a distribution of fluorescence intensities of light converged by an objective lens immediately above the origin, using a confocal system where a fluorescent light source covers the entire areas of the x- and y-planes at an equal intensity. The graph shows a normal distribution where the intensities are normalized with respect to the value at the origin. The half-width is 10 $\mu$m. Herein, since the size of the spot on the biochip is 10 $\mu$m×10 $\mu$m, the average intensity within the range of (x, y)=(−5 to 5, −5 to 5) is the fluorescent intensity originating from the target spot, and the average intensity within the range of (x, y)=(5 to 15, −5 to 5) is the fluorescent intensity originating from the adjacent spot. The proportion of the fluorescent intensity originating from the adjacent spot to the fluorescent intensity from the target spot is 18.91%, and the proportion of the fluorescent intensity originating from the spot two spots away from the target spot is 0.04%.

When the scanning speed of the reading head 11 in the x-direction is 1.25 m/s, the head travels between adjacent spots (10 $\mu$m) in 8 $\mu$s. Based on the attenuation waveform of fluorescence shown in FIG. 3, the proportion of the remaining fluorescent intensity within 8 $\mu$s is 91.49%, and 83.71% when the head 11 travels for a distance of two spots (i.e., 16 $\mu$s). In view of this fluorescence attenuation with respect to time, the proportions of residual fluorescence contained in the fluorescence of the target spot are 17.30% from the preceding spot that has just been scanned and 0.03% for the spot two spots away from the target spot. Therefore, according to the conventional fluorescence reading technique where fluorescence from the spots lining in the x-direction are read sequentially, the S/N ratio will be about 5.8, which has no advantage of using the time-resolved fluorescence. According to the present invention, in order to minimize the effect of the residual fluorescence from the adjacent spot, the scanning with the reading head 11 has been devised.

Figure 5:
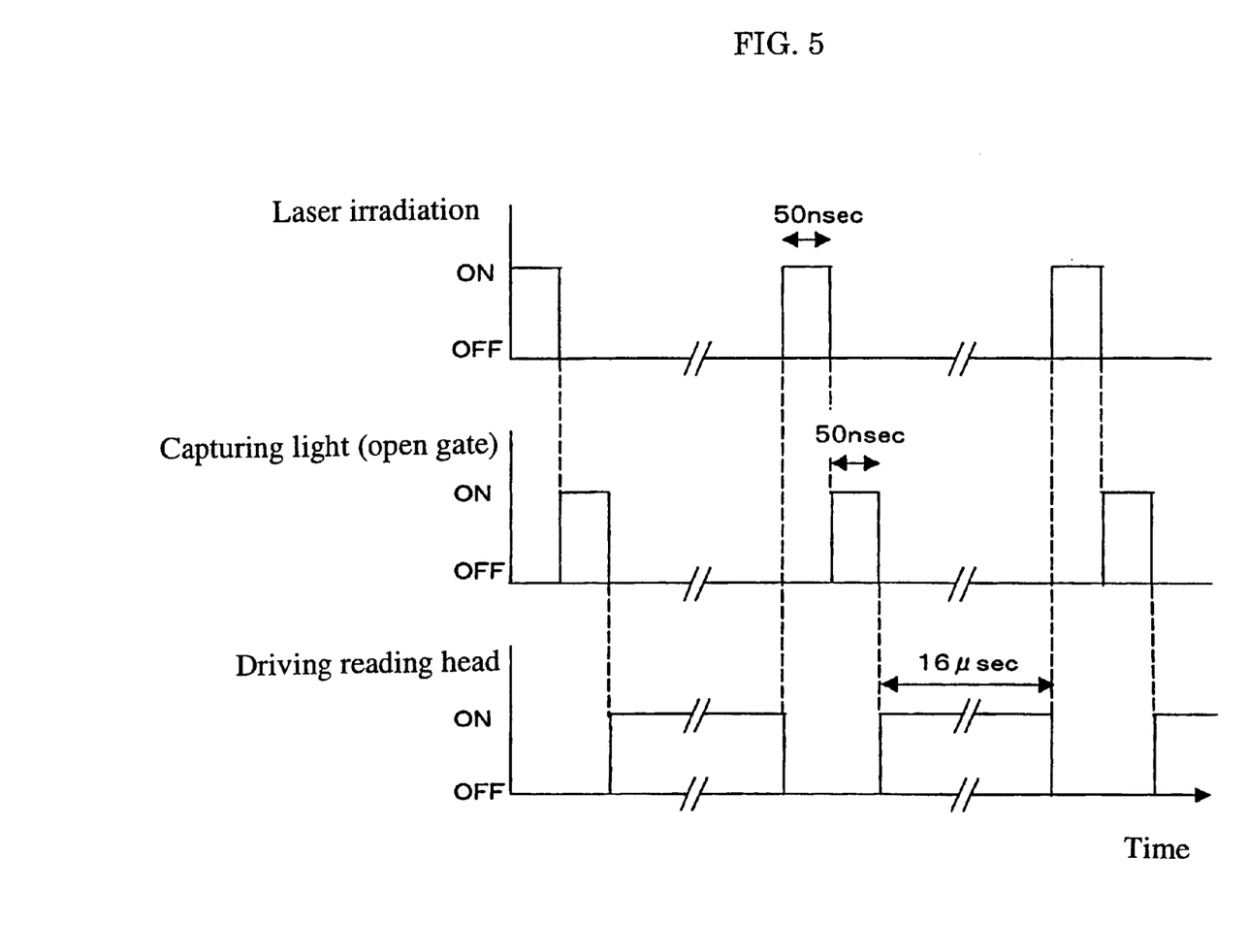
FIG. 5 is a diagram showing timings of laser beam irradiation, fluorescence capture and for driving the head.

Hereinafter, a fluorescence reading method according to the present invention will be described with reference to FIGS. 5 and 6A to 6G. FIG. 5 is a diagram showing timings of laser beam irradiation, fluorescence capture and driving of the reading head. FIGS. 6A to 6G are schematic diagrams for illustrating the order for reading spots according to the present invention. In FIG. 6, a black dot represents a spot whose fluorescence has been read, while a white dot represents a spot whose fluorescence has not yet been read.

As shown in FIG. 5, the reading head 11 is driven intermittently in the x-direction and stopped above, for example, every second spots. While the reading head 11 is stopped, laser beam irradiation and time-resolved fluorescence reading take place. The time-resolved fluorescence reading is performed for gated output signals from the gated photomultiplier 6. This reading is performed after the laser beam irradiation to avoid the influence of the excitation laser beam.

Figure 6A:
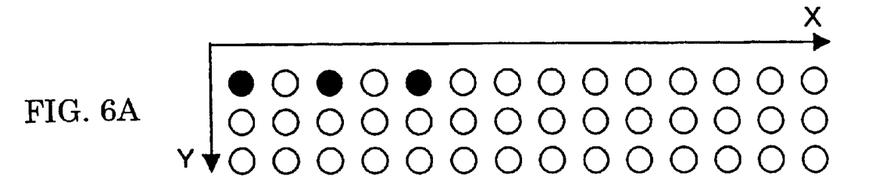
FIGS. 6A to 6G are diagrams for illustrating an order for reading spots according to the present invention.
Figure 6B:
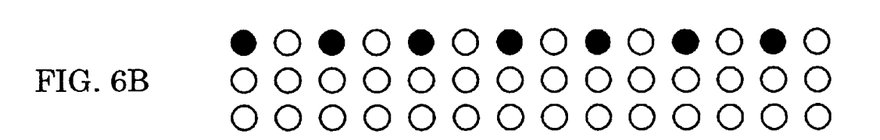
Figure 6C:
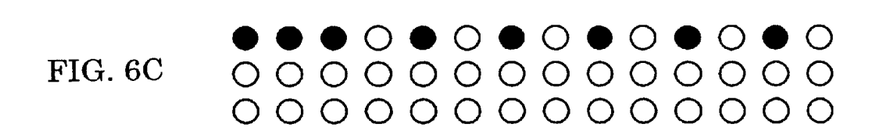
Figure 6D:
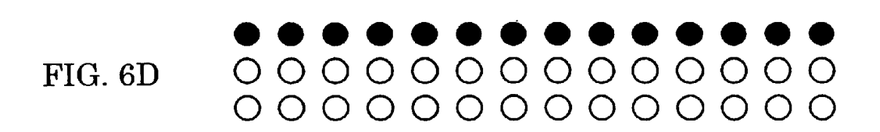

FIGS. 6A to 6G schematically show the arrangement of spots on the biochip and the order of spot reading. Here, the position of a spot which is "m"th to the x-direction and "n"th to the y-direction is represented as (m, n). In this example, as shown in FIGS. 6A and 6B, fluorescence is read for every second spots as (1, 1), (3, 1), (5, 1) and so on. By skipping every second spots in the x-direction upon fluorescence reading, no harm effect is caused by the time-resolved fluorescence originating from the spot that has just been excited. As shown in FIG. 6B, when the reading head has finished scanning the end of the line, the reading head 11 travels back towards the top of the same line to a spot that is shifted for 1 spot from the first read spot (1, 1) in the x-direction (i.e., spot (2, 1)). As shown in FIGS. 6C and 6D, the same operation is repeated at same intervals. In other words, this time, the spots are read in the order of (2, 1), (4, 1), (6, 1) and so on. Consequently, all of the spots on this line are completely scanned by being scanned twice.

Figure 6E:
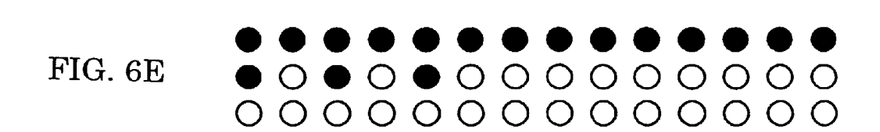
Figure 6F:
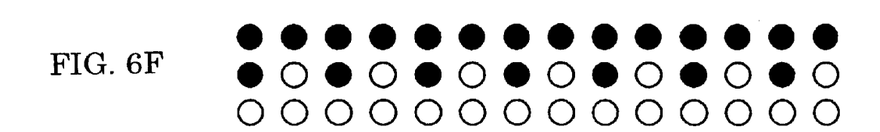
Figure 6G:
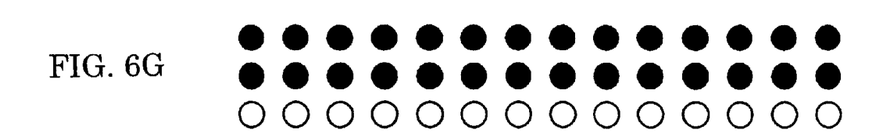

Next, the y-direction driving motor 3 drives the stage 21 to send the biochip 1 for 1 spot in the y-direction with respect to the reading head 11. Similarly, as shown in FIGS. 6E and 6F, fluorescence reading for the second line is performed for every second spots in the x-direction as (1, 2), (3, 2), (5, 2) and so on. Then, traveling back towards the top of the second line, the head 11 performs fluorescence reading for the remaining spots (2, 2), (4, 2), (6, 2) and so on as shown in FIG. 6G. This operation is repeated for the entire spots on the chip. According to this fluorescence reading method, S/N ratio increases to about 3000. However, the time required to complete the fluorescence reading for the entire spots is approximately doubled.

This skip reading according to the present invention is useless for Cy3 fluorescence label since the fluorescence duration of Cy3, i.e. 1.3 ns, is fairly short (see FIG. 3) for the time of the reading head 11 to travel to the adjacent spot (i.e., 8 $\mu$s). The conventional sequential scanning can be employed for reading a time-resolved fluorescence to obtain a high S/N ratio by extending the time of transferring the head between the spots to suit the fluorescence duration of the time-resolved fluorescence. However, since the duration of europium (400 $\mu$s) is fifty times longer than the time for the reading head to travel in the conventional manner (8 $\mu$s), fluorescence reading takes time that is about 25 times longer than that according to the method of the present invention. The time required for fluorescence reading is 5 minutes for conventional Cy3 reading, 10 minutes according to the present invention, and up to 250 minutes according to the conventional method employing the time-resolved fluorescent substance, which is obviously unpractical.

By employing the method of the present invention for reading a time-resolved fluorescence, the S/N ratio can be greatly increased than a conventional reading method without greatly increasing the reading time.

According to the present invention, residual fluorescence noise of a time-resolved fluorescence owing to the length of the half-life of the fluorescent intensity characteristic of the time-resolved fluorescence can be greatly reduced to prevent it from interfering with the adjacent area, thereby obtaining data at a high S/N ratio.

What is claimed is:

1. A method for reading fluorescence by radiating excitation light on a plurality of spots arranged at predetermined intervals each containing a substance labeled with a time-resolved fluorescent substance and detecting fluorescence generated from each of the plurality of spots, the method comprising:

a first step of irradiating a first spot with excitation light for a predetermined time;

a second step of detecting fluorescence generated from the first spot after the irradiation with the excitation light;

a third step of irradiating a second spot with excitation light, which is distanced from the first spot by a distance that is two or more times the distance between adjacent spots; and a fourth step of detecting fluorescence generated from the second spot after the irradiation with the excitation light, wherein, the third and fourth steps are repeated to detect fluorescence from all of the spots.

2. A method for reading fluorescence according to claim 1, wherein the substance labeled with the time-resolved fluorescent substance is a biological substance.

3. A method for reading fluorescence by radiating excitation light on a plurality of spots arranged in a line at predetermined intervals each containing a substance labeled with a time-resolved fluorescent substance and detecting fluorescence generated from each of the plurality of spots, wherein an operation of radiating excitation light to a spot for a predetermined time and thereafter detecting fluorescence generated from the spot is performed sequentially for every nth spots (where n is an integer of 2 or higher), and when the operation reaches the end of the line, the operation goes back towards the top of the line and is repeated for every nth spots (where n is an integer of 2 or higher) starting from a spot that has not yet undergone fluorescence detection.

4. A method for reading fluorescence according to claim 3, wherein the substance labeled with the time-resolved fluorescent substance is a biological substance.

5. A method for reading fluorescence by radiating excitation light on a plurality of spots arranged in a line at predetermined intervals each containing a substance labeled with a time-resolved fluorescent substance and detecting fluorescence generated from each of the plurality of spots, wherein an operation of radiating excitation light to a spot for a predetermined time and thereafter detecting fluorescence generated from the spot is performed sequentially for every second spots, and when the operation reaches the end of the line, the operation goes back towards the top of the line and is repeated for the remaining spots.

6. A method for reading fluorescence according to claim 5, wherein the substance labeled with the time-resolved fluorescent substance is a biological substance.

7. An apparatus for reading fluorescence by detecting fluorescence from a plurality of spots arranged on a substrate each containing a substance labeled with a time-resolved fluorescent substance, the apparatus comprising:
- a stage for holding the substrate;
- a laser light source;
- a reading head movable in a two-dimensional manner relative to the substrate, the reading head provided with an excitation light optical system for irradiating the spots on the substrate with a laser beam emitted from the laser light source and a light capturing optical system for capturing fluorescence generated from the spots;
- an optical detector for detecting fluorescence captured by the light capturing optical system;
- a driver for driving the stage and the reading head relative to each other; and
- a controller for controlling the laser light source, the light detector and the driver,
- wherein the controller controls the driver such that the reading head is aligned above each of the spots on the substrate in a skipping manner, and controls the laser light source and the light detector such that a spot below the reading head is irradiated with a laser beam for a predetermined time and thereafter fluorescence generated from the irradiated spot is detected.

8. An apparatus for reading fluorescence according to claim 7, wherein the irradiation light optical system and the light capturing optical system form a confocal optical system.

9. An apparatus for reading fluorescence according to claim 8, wherein the driver comprises a reading head driver for driving the reading head in one direction, and a stage driver for driving the stage in a direction generally perpendicular to the driving direction of the reading head.

10. An apparatus for reading fluorescence according to claim 9, wherein the substrate is a biochip provided with a plurality of spots containing biological substances labeled with a time-resolved fluorescent substance.

11. An apparatus for reading fluorescence according to claim 8, wherein the substrate is a biochip provided with a plurality of spots containing biological substances labeled with a time-resolved fluorescent substance.

12. An apparatus for reading fluorescence according to claim 7, wherein the driver comprises a reading head driver for driving the reading head in one direction, and a stage driver for driving the stage in a direction generally perpendicular to the driving direction of the reading head.

13. An apparatus for reading fluorescence according to claim 12, wherein the substrate is a biochip provided with a plurality of spots containing biological substances labeled with a time-resolved fluorescent substance.

14. An apparatus for reading fluorescence according to claim 7, wherein the substrate is a biochip provided with a plurality of spots containing biological substances labeled with a time-resolved fluorescent substance.

* * * * *